US011690675B2

(12) United States Patent
Mirdo et al.

(10) Patent No.: US 11,690,675 B2
(45) Date of Patent: *Jul. 4, 2023

(54) INTERACTIVE ANTERIOR-POSTERIOR AXIS DETERMINATION

(71) Applicant: Smith & Nephew, Inc., Memphis, TN (US)

(72) Inventors: Stephen Mirdo, Memphis, TN (US); Yangqiu Hu, San Antonio, TX (US)

(73) Assignee: SMITH & NEPHEW, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/558,828

(22) Filed: Dec. 22, 2021

(65) Prior Publication Data

US 2022/0110689 A1    Apr. 14, 2022

Related U.S. Application Data

(63) Continuation of application No. 16/940,968, filed on Jul. 28, 2020, now Pat. No. 11,207,138, which is a continuation of application No. 16/597,478, filed on Oct. 9, 2019, now Pat. No. 10,751,130, which is a continuation of application No. 15/641,893, filed on Jul. 5, 2017, now Pat. No. 10,555,774.

(Continued)

(51) Int. Cl.
*A61B 34/10* (2016.01)
*G16H 50/50* (2018.01)

(52) U.S. Cl.
CPC .............. *A61B 34/10* (2016.02); *G16H 50/50* (2018.01); *A61B 2034/108* (2016.02)

(58) Field of Classification Search
CPC ...... A61B 34/10; A61B 2034/101–108; G06T 2207/30004
See application file for complete search history.

(56) References Cited

U.S. PATENT DOCUMENTS

| 7,155,042 B1* | 12/2006 | Cowan | G06T 7/66 |
| | | | 382/128 |
| 2010/0312096 A1* | 12/2010 | Guttman | A61B 34/25 |
| | | | 600/411 |
| 2016/0008143 A1* | 1/2016 | Mahfouz | A61F 2/4684 |
| | | | 606/102 |

OTHER PUBLICATIONS

Cerveri, Pietro, et al. "Determination of the Whiteside line on femur surface models by fitting high-order polynomial functions to cross-section profiles of the intercondylar fossa." Computer Aided Surgery 16.2 (2011): 71-85. (Year: 2011).*

* cited by examiner

*Primary Examiner* — Ryan McCulley
(74) *Attorney, Agent, or Firm* — KDW Firm PLLC

(57) ABSTRACT

A process according to certain embodiments includes generating a distal femur model including an intercondylar surface model, receiving information related to user-selected points on the intercondylar surface model, generating a datum line extending between the points, generating an axis line, and determining an AP axis based upon the axis line. Generating the axis line includes performing an axis line procedure including generating a plurality of planes along the datum line, generating a plurality of contours at intersections between the intercondylar surface model and the planes, generating saddle points at local extrema of the contours, and fitting the axis line to the saddle points. The process may further include generating an updated datum line based upon the axis line, and performing a subsequent iteration of the axis line procedure using the updated datum line.

28 Claims, 10 Drawing Sheets

Related U.S. Application Data

(60) Provisional application No. 62/358,319, filed on Jul. 5, 2016.

INTERACTIVE ANTERIOR-POSTERIOR AXIS DETERMINATION

CROSS-REFERENCE TO RELATED APPLICATIONS

This application is a continuation of U.S. patent application Ser. No. 16/940,968, filed on Jul. 28, 2020, which is a continuation of U.S. patent application Ser. No. 16/597,478, filed on Oct. 9, 2019, issued as U.S. Pat. No. 10,751,130, which is a continuation of U.S. patent application No. 15/641,893,filed on Jul. 5, 2017, issued as U.S. Pat. No. 10,555,774, which claims the benefit of priority to U.S. Provisional Application No. 62/358,319, filed on Jul. 5, 2016, each of which is incorporated herein by reference in its entirety.

TECHNICAL FIELD

The present disclosure generally relates to determining an anterior-posterior axis of a bone, and more particularly but not exclusively relates to determining an anterior-posterior axis of a distal femur.

BACKGROUND

Certain techniques for planning orthopedic surgical procedures involve utilizing patient-specific information, such as a model of a bone, to accurately determine various parameters for a customized surgical procedure and/or customized orthopedic implant. Such techniques may involve determining an optimal orientation of the bone model based on one or more axes of the bone model. For example, a technique for planning a knee replacement procedure may include determining the optimal orientation of a distal femur model based on the anterior-posterior (AP) axis, the transepicondylar axis (TEA), and/or the posterior condylar axis (PCA).

One metric that is widely recognized as an important predictor for the outcome of total knee replacement surgeries is the varus-valgus alignment of the knee. Due to the fact that the rotation about the AP axis determines the varus-valgus angle, accurate determination of the AP axis plays an important role in the planning process. Rotation of the model about an inaccurate AP axis may result in a flawed or sub-optimal plan, thereby leading to surgical outcomes that are less than ideal. One difficulty that may arise in the planning procedure stems from the fact that the feature points utilized in determining the AP axis are generally less well-defined than those utilized in determining the TEA and PCA, leading to a greater degree of subjectivity and variability in the determination of the AP axis. In certain conventional procedures, the AP axis is subjectively determined by an operator manually estimating or "eyeballing" the axis, a technique that may suffer from variability between the axes determined for a single model, whether by the same operator or different operators. For these reasons among others, there remains a need for further developments in this technological field.

SUMMARY

In certain embodiments, a process may include generating a distal femur model including an intercondylar surface model, receiving information related to user-selected points on the intercondylar surface model, generating a datum line extending between the points, generating an axis line, and determining an AP axis based upon the axis line. Generating the axis line may include performing an axis line procedure including generating a plurality of planes along the datum line, generating a plurality of contours at intersections between the intercondylar surface model and the planes, generating saddle points at local extrema of the contours, and fitting the axis line to the saddle points. The process may further include generating an updated datum line based upon the axis line, and performing a subsequent iteration of the axis line procedure using the updated datum line. Further embodiments, forms, features, and aspects of the present application shall become apparent from the description and figures provided herewith.

DETAILED DESCRIPTION OF ILLUSTRATIVE EMBODIMENTS

Figure 1:
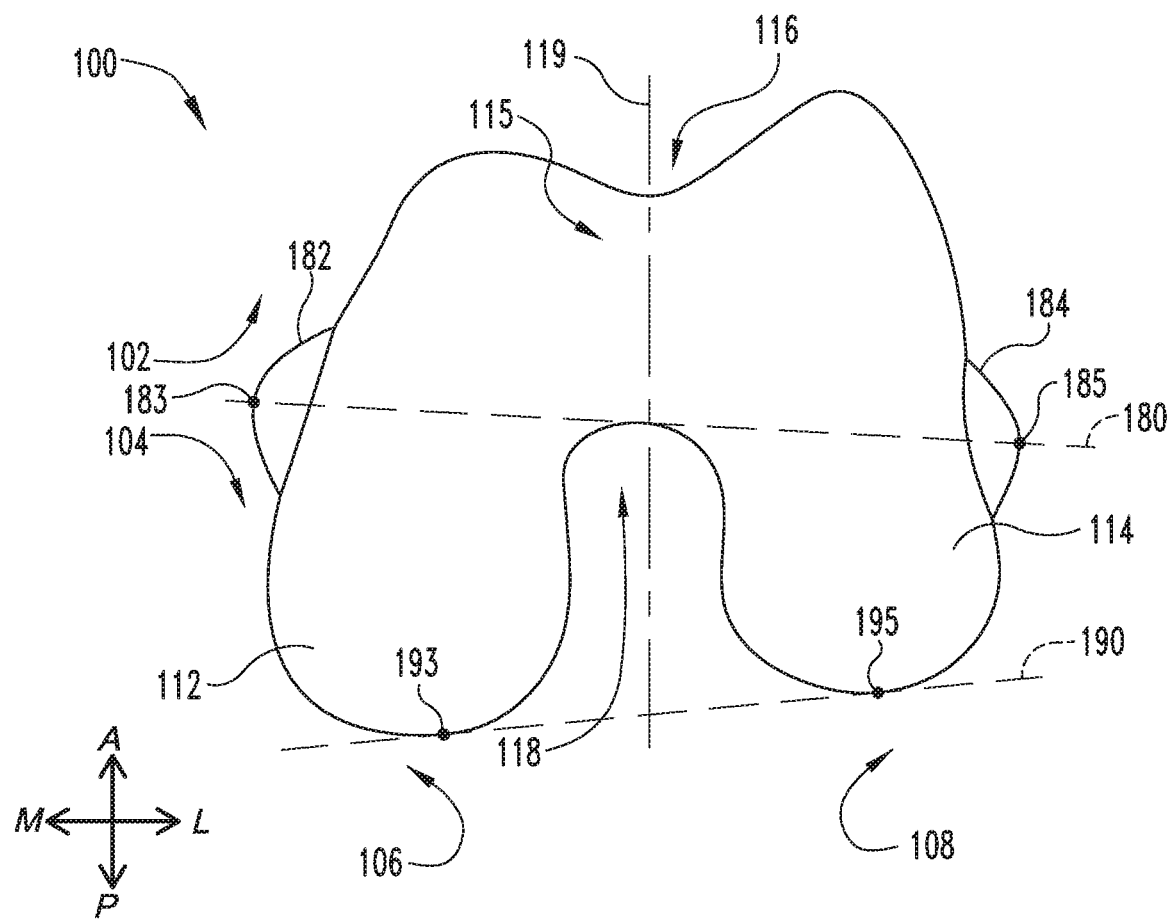
FIG. 1 is an end view of a distal femur.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates a distal femur 100 having an anterior region 102, a posterior region 104, a medial region 106, and a lateral region 108. The distal femur 100 includes a medial condyle 112, a lateral condyle 114, and an intercondylar region 115 including a trochlear groove 116 and a trochlear notch 118. The distal femur 100 also has an anterior-posterior (AP) axis 119, a transepicondylar axis (TEA) 180, and a posterior condylar axis (PCA) 190. The AP axis 119 extends through the intercondylar region 115, and may be identified using the techniques described herein. The TEA 180 generally extends between the medial epicondyle 182 and the lateral epicondyle 184, and may be defined along a line extending between a medial point 183 on the medial epicondyle 182 and a lateral point 185 on the lateral epicondyle 184. The PCA 190 generally extends along a posterior or distal side of the distal femur 100, and may be defined along a line extending between a medial distal point 193 on the medial condyle 112 and a lateral distal point 195 on the lateral condyle 114. As noted above, in certain orthopedic procedures, it may be desirable or necessary to accurately determine the AP axis 119, the TEA 180, and/or the PCA 190 in order to achieve optimal results for the surgery.

Figure 2:
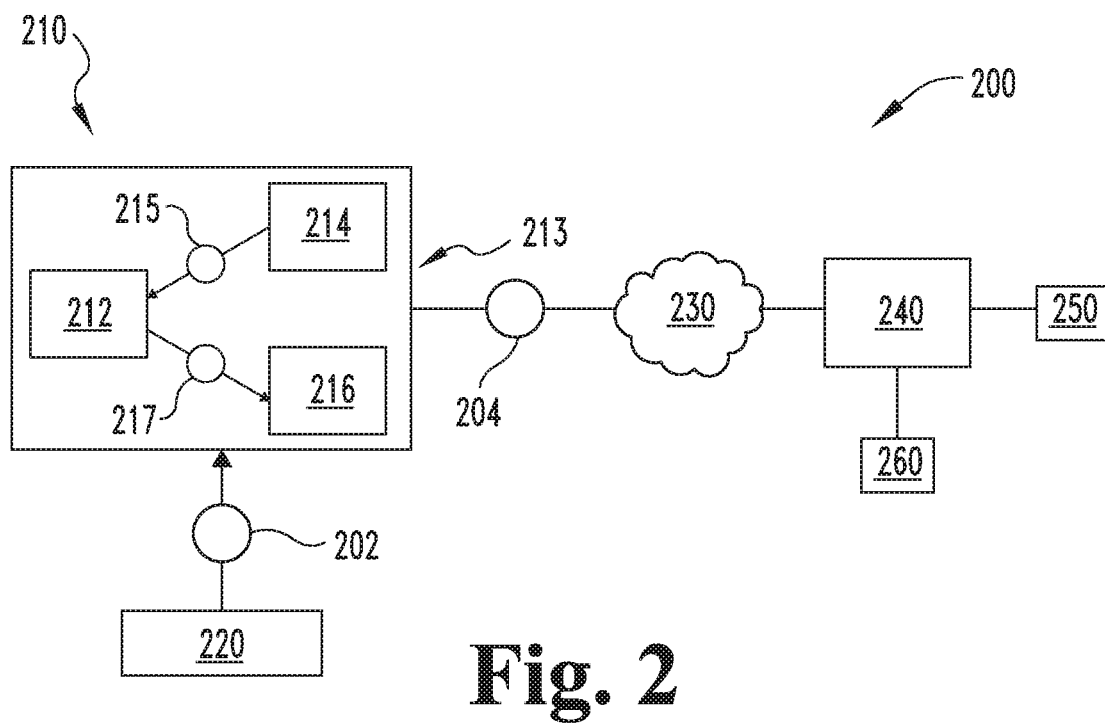
FIG. 2 is a schematic illustration of a system according to certain embodiments.

FIG. 2 illustrates a system 200 according to certain embodiments. The system 200 includes a design device 210, a design tool 220 in communication with the design device 210, a network 230 in communication with the design device 210, a server 240 in communication with the network 230, modeling tools 250 accessible by the server 240, and a memory 260. An example of a computing device 500 which may be utilized in connection with one or more of the elements of the system 200 is described below with reference to FIG. 10. Although FIG. 2 illustrates the various elements of the system 200 as discrete but connected elements, it is to be understood that one or more of the elements may be combined with another element or distributed among a plurality of the other elements. For example, while the memory 260 is illustrated as being in communication with the server 240, it is also contemplated that the memory 260 may be provided at the design device 210 and/or distributed across the network 230. Additionally, unless specified to the contrary, one or more of the illustrated elements may be omitted, and one or more elements that are not specifically illustrated in FIG. 2 may be included in the system 200.

The design device 210 is accessible by a user, such as a surgeon or a surgical planner, to enable the user to interact with the design device 210 and to enable the system 200 to perform one or more of the actions and operations described hereinafter. As examples, the design device 210 may be provided as a desktop computer, a laptop computer, a personal data assistant (PDA), a mobile handheld device, or a dedicated device. The design device 210 includes a processor 212, and may further include a user interface 213 including an input device 214 and/or a display device 216. The input device 214 may be any form of input operable to convert actions by a user into signals representative of input information 215. By way of example, the input device 214 may include one or more of a keyboard, a keypad, a touchpad, a mouse, a touchscreen, a camera, and/or a motion detector. Similarly, the display device 216 may be any form of display operable to convert output information 217 received from the processor 212 into a form identifiable to the user. By way of example, the display device 216 may include one or more of a monitor, a projector, a video screen, and/or a tactile interface. In certain embodiments, the user interface 213 may combine the input device 214 and the display device 216 in a single integral unit, such as a touchscreen. In certain embodiments, the user interface 213 may include plural input devices 214 and/or plural display devices 216, which may be located at separate locations.

The design tool 220 is accessible by the design device 210 to enable the tool 220 to provide patient information 202 to the design device 210. The tool 220 may be provided at the design device 210, or may be provided elsewhere, such as at the server 240. The patient information 202 may include diagnostic data, such as a digital X-ray image, a magnetic resonance image (MRI), or a computer tomography (CT) image. In certain embodiments, the information 202 may be representative of a model of at least a portion of the patient's anatomy. In certain embodiments, the tool 220 may enable the user to select certain points or elements associated with the information, such as points on the model. The tool 220 may enable the user to manipulate the image shown on the display device 216. For example, the system 200 may be configured to display the model on the display device 216, and the tool 220 may enable the user to zoom, translate, and/or rotate the model. In certain embodiments, the user interface 213 may include the tool 220, and/or the tool 220 may include one or both of the input device 214 and the display device 216.

The server 240 may, for example, be embodied as a computer. The server 240 may be enabled to receive and transmit information 204 between the surgeon's design device 210 and other elements of the system 200. Transmission of the information 204 may be performed over the network 230, which may be embodied as the Internet or as an intranet. The server 240 may be provided with modeling tools 250 which generate certain responses to information 204 received from the design device 210. In some embodiments, the tools 250 may include computer aided design (CAD) systems. Common CAD systems known in the art include SolidWorks® (produced by SolidWorks Corporation, 300 Baker Avenue, Concord, Mass. 01742) and Pro Engineer® (produced by Parametric Technology Corporation, 140 Kendrick Street, Needham, Mass. 02494). The CAD systems may be enabled to translate information 204 received from the design device 210 into a model or a modified model. For example, the CAD systems may generate an initial model based upon the patient information 202, and generate modifications of the model based upon the input information 215.

Figure 3A:
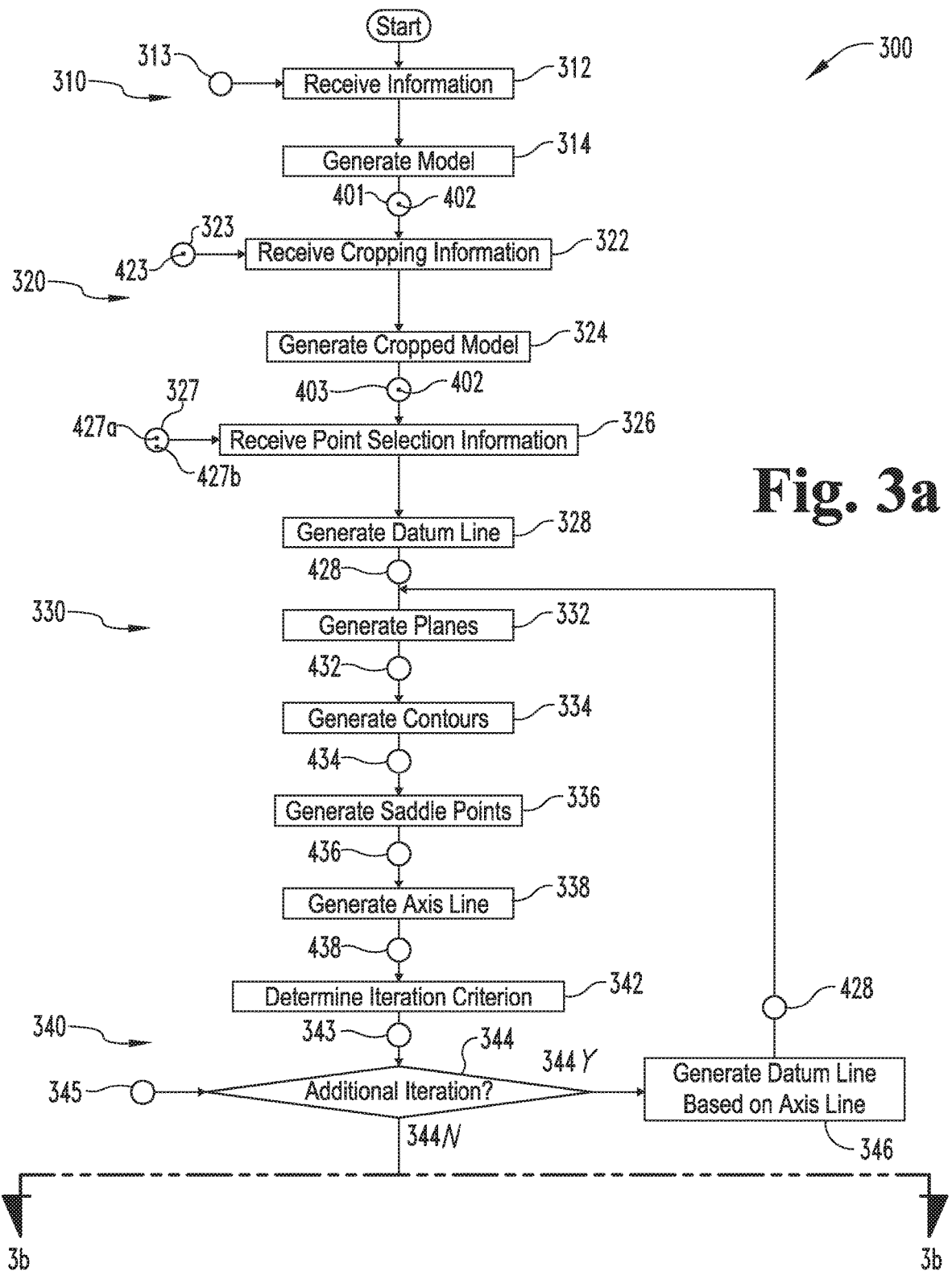
FIGS. 3*a* and 3*b* illustrate a schematic flow diagram of a process according to certain embodiments.
Figure 3B:
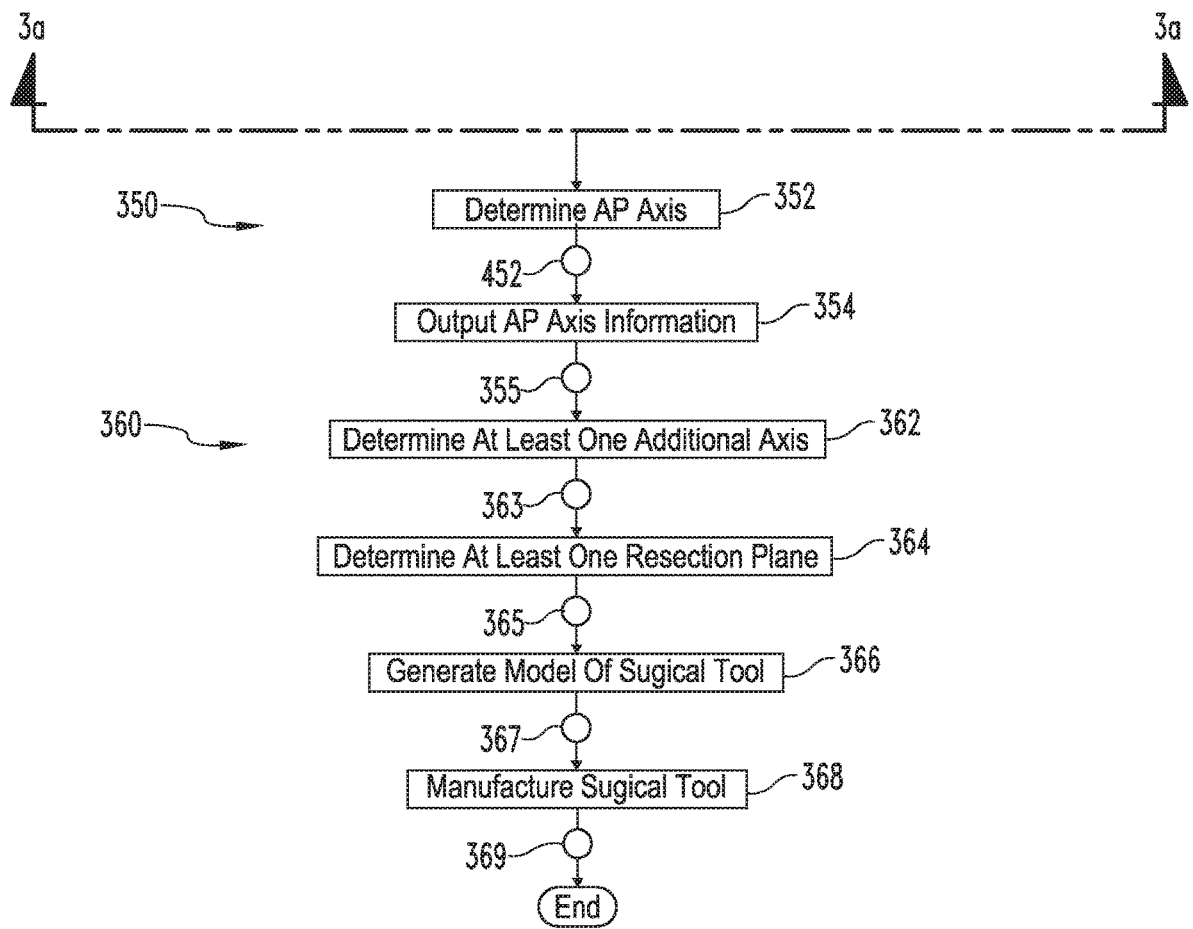

With additional reference to FIGS. 3-9, further details regarding a process according to certain embodiments will now be provided. FIG. 3 illustrates an embodiment of a process 300 for determining the AP axis 119 of the distal femur 100 of a particular patient, and FIGS. 4-9 illustrate exemplary stages of the process 300. Operations illustrated for the processes in the present application are understood to be examples only, and operations may be combined or divided, and added or removed, as well as re-ordered in whole or in part, unless explicitly stated to the contrary. Unless specified to the contrary, it is contemplated that certain operations, procedures, or steps performed in the process 300 may be performed wholly by the design device 210, the design tool 220, the network 230, the server 240, or the modeling tools 250, or that the operations or steps may be distributed among one or more of the elements of the system 200 and/or additional devices or systems which are not specifically illustrated in FIG. 2.

In the illustrated form, the process 300 generally includes a modeling procedure 310, a parameter procedure 320, an axis line procedure 330, an iterative procedure 340, and an AP axis procedure 350, and may further include a surgical tool procedure 360. Generally speaking, the modeling procedure 310 involves generating a distal femur model 400, and the parameter procedure 320 involves defining parameters and criteria related to the model 400. The axis line procedure 330 generally involves generating an axis line 438 based upon defined parameters and criteria, the iterative procedure 340 generally involves determining whether to perform additional iterations of the axis line procedure 330, and the AP axis procedure 350 generally involves determining an AP axis 452 based upon the axis line 438 generated in a selected iteration of the axis line procedure 330. The surgical tool procedure 360 generally includes designing and optionally manufacturing a patient-specific surgical tool 369 based in part upon the generated AP axis 452.

The modeling procedure 310 may begin with an operation 312, which includes receiving information 313 relating to the distal femur 100 of a particular patient. In certain embodiments, the received information 313 may include diagnostic data, such as a digital X-ray image, an MRI, or a CT image. In other embodiments, the received information 313 may be information relating to a model of the distal femur 100, such as a CAD model. In certain embodiments, the information 313 may include patient information 202 provided by the tool 220, and the operation 312 may include receiving the patient information 202 at the design device 210. In certain embodiments, the patient information 202 may include model data defining the model 400.

The modeling procedure 310 may continue to an operation 314, which includes generating a three-dimensional model 400 (e.g., a CAD model) of the distal femur 100 based upon the received information 313. In embodiments in which the received information 313 relates to the distal femur model 400, the model 400 may be generated based upon the received information 313 relating to the model 400. In embodiments in which the received information 313 relates to diagnostic imaging data, the operation 314 may include generating the model 400 by segmenting or otherwise processing the imaging data to reconstruct the geometry and shape, or otherwise define the relevant surfaces and other morphological aspects of the distal femur 100. For example, individual image slices of MRI data may be processed to identify boundaries between the distal femur 100 and the surrounding anatomy. Such segmenting may be accomplished by manual, automated, or semi-automated processes. In some embodiments, segmentation may be facilitated by software packages available from, for instance, Able Software Corp of Lexington, Mass. (3D-DOCTOR™), Materialise of Leuven, Belgium (MIMICS®) or other software. In some embodiments, other techniques may be used to process imaging data, such as threshold based image processing, probabilistic atlas based, statistical shape modeling based, or other techniques. Some embodiments may at least partially utilize MATLAB® based processes (of Math-Works, Inc., Natick, Mass.) as part of such techniques.

Figure 4:
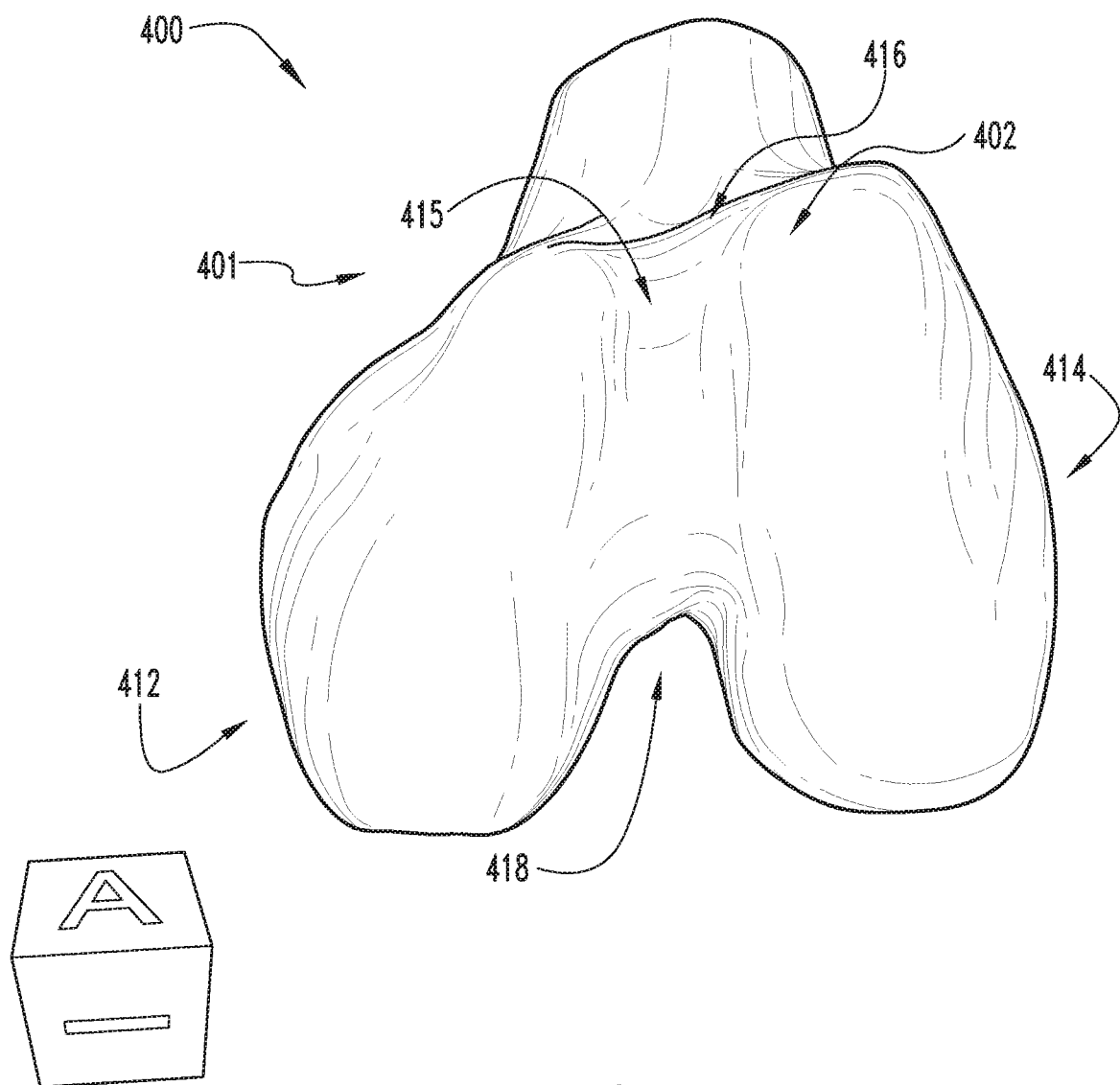
FIG. 4 illustrates a model of a distal femur.

The distal femur model 400 may include a surface model 401 representative of the surface of the distal femur 100 of the particular patient. The surface model 401 may include an intercondylar surface model 402 representative of the surface of the intercondylar region 115 of the distal femur 100 of the particular patient. The operation 314 may further include displaying the distal femur model 400 on the display device 216, for example as illustrated in FIG. 4.

The process 300 may continue to the parameter procedure 320, which may begin with an operation 322. The operation 322 includes receiving cropping information 323 relating to a user-selected portion 123 of the distal femur 100. As described in further detail below, the cropping information 323 is used to generate a cropped model 403 representative of the user-selected portion 123 based upon the model 400 representative of the distal femur 100. Additionally, the user-selected portion 123 includes at least a portion of the intercondylar region 115, such that the cropped model 403 includes at least a portion of the intercondylar surface model 402. The cropping information 323 may be received via the user interface 213 and/or the tool 220 in an interactive manner. For example, the distal femur surface model 401 may be displayed on the display device 216, and the user may generate a three-dimensional selection box 423 (FIG. 5) about the selected portion 123 using the input device 214. In certain forms, the operation 322 may include prompting the user to generate the selection box 423, for example by generating a visual prompt at the display device 216.

Figure 5:
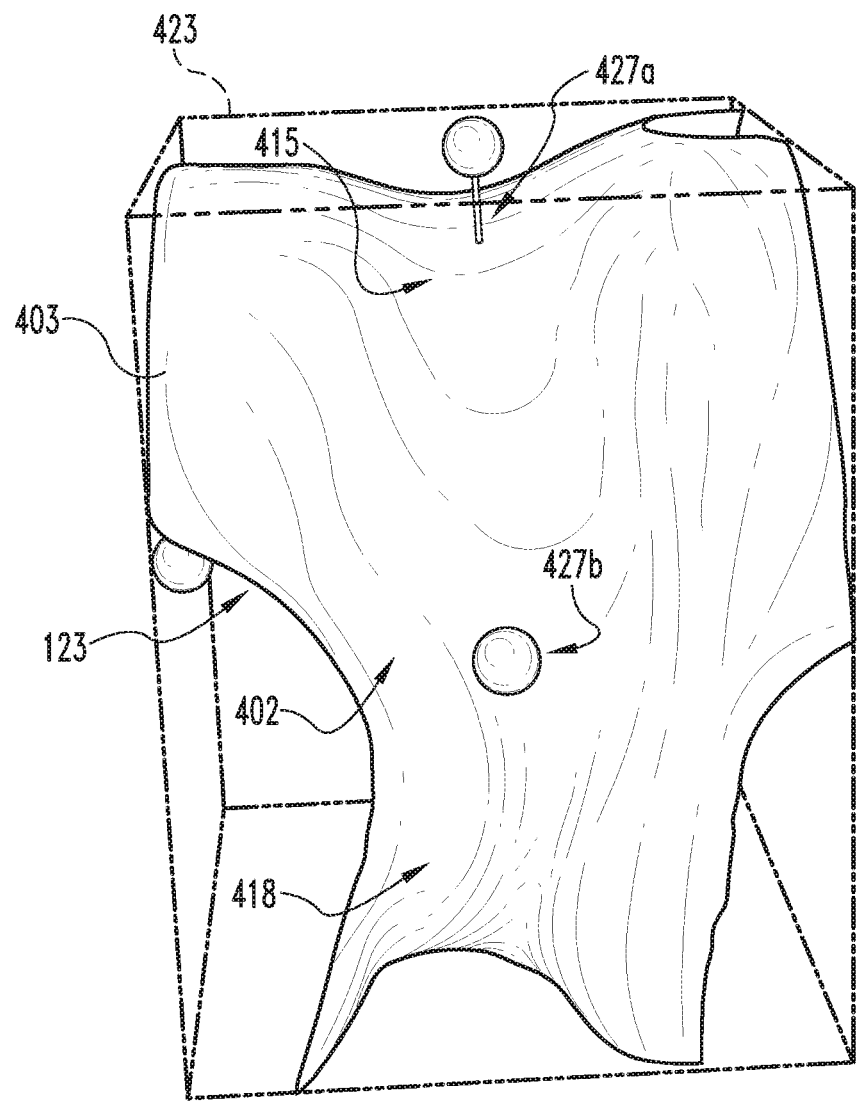
FIG. 5 illustrates a portion of the model illustrated in FIG. 4 along with a cropping box and a pair of user-selected points.
Figure 5:
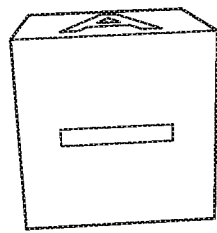

Upon receiving the cropping information 323, the parameter procedure 320 may continue to an operation 324, which includes generating a model 403 of at least a portion of the distal femur 100. More specifically, the operation 324 may include generating a revised or cropped model 403 that is representative of the selected portion 123 and includes at least a portion of the intercondylar surface model 402. The operation 324 may, for example, include cropping the distal femur surface model 401 to remove portions of the surface model 401 that are outside of the boundaries defined by the selection information 323 (e.g., the boundaries of the selection box 423). The operation 324 may further include displaying the cropped model 403 along with the selection box 423, for example as illustrated in FIG. 5.

The parameter procedure 320 may continue to an operation 326, which includes receiving point selection information 327 relating to user-selected first and second points 427a, 427b on the intercondylar surface model 402. In certain forms, the points 427a, 427b may relate to an initial estimate of the AP axis of the femur 100. For example, the operation 326 may include displaying the cropped model 403 on the display device 216, and prompting the user to estimate the AP axis by selecting points 427a, 427b on the intercondylar surface model 402 using the input device 214. The operation 326 may further include displaying the cropped model 403 along with the selected points 427a, 427b, for example as illustrated in FIG. 5.

Figure 6:
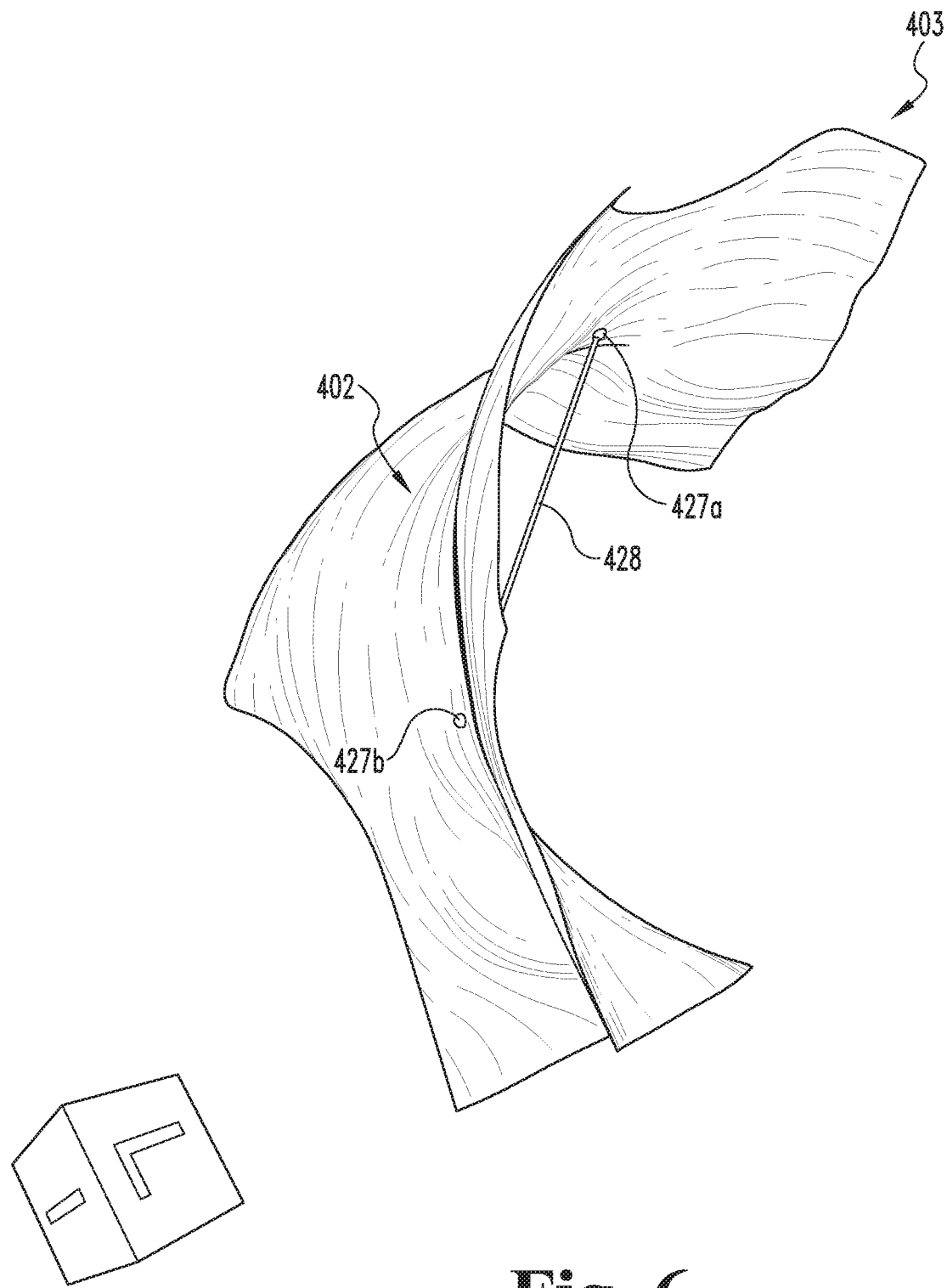
FIG. 6 illustrates the cropped model of FIG. 4 with a datum line extending between the user-selected points.

After the points 427a, 427b have been selected, the procedure 320 may continue to an operation 328, which includes generating a datum line 428 based upon the point selection information 327 such that the datum line 428 extends between the selected points 427a, 427b. The operation 328 may further include displaying the datum line 428 along with the cropped model 403 and/or the selected points 427a, 427b, for example as illustrated in FIG. 6. In certain forms, the datum line 428 may be representative of the user's initial estimate for the AP axis 119, for example in embodiments in which points 427a, 427b are selected based upon the user's initial estimate for the AP axis 119. In such forms, the operation 328 may further include prompting the user to confirm the initial estimate represented by the datum line 428, and selectively returning to the operation 326 to enable the user to revise the estimate by providing new point selection information 327.

Figure 7:
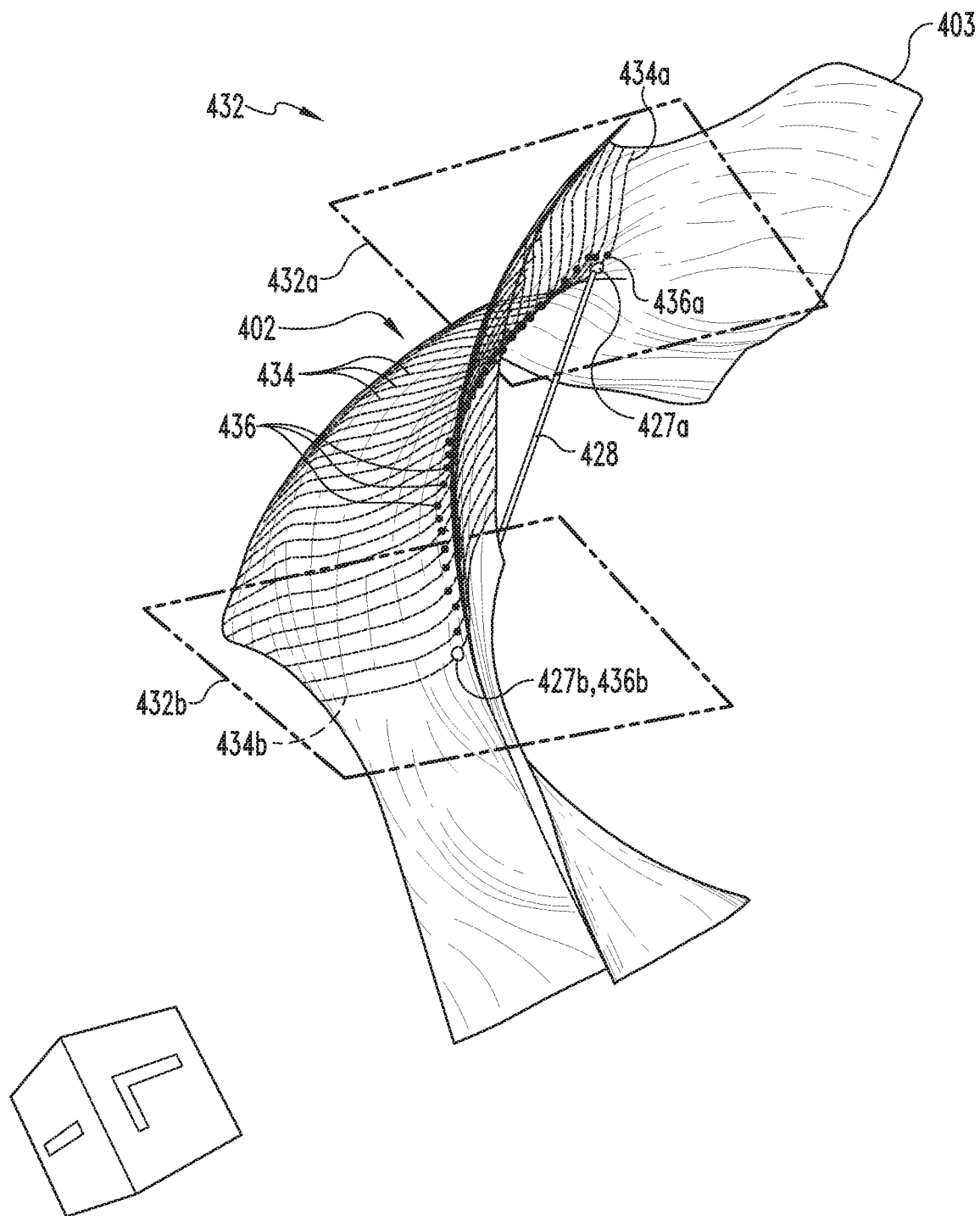
FIG. 7 illustrates the cropped model and datum line of FIG. 6 along with planes, contours, and saddle points.

After generating and optionally displaying the datum line 428, the process 300 may continue to the axis line procedure 330, which includes an operation 332. The operation 332 includes generating a plurality of planes 432 that define a predetermined plane angle with respect to the datum line 428, and which intersect the intercondylar surface model 402. While other forms are contemplated, in the illustrated embodiment, the planes 432 are orthogonal to the datum line 428. For example, FIG. 7 illustrates planes 432a, 432b which are orthogonal to the datum line 428 and which intersect the datum line 428 at the user-selected points 427a, 427b. In the interest of clarity, only two planes 432 are illustrated in FIG. 7. It is to be understood, however, that additional planes 432 may be defined at constant or varying offset intervals along the datum line 428.

For reasons which will become apparent, the offset interval between adjacent planes 432 defines the granularity of the axis line procedure 330, and the computational requirements for the procedure 330 may be inversely proportional to the granularity. A greater value for the offset interval results in fewer planes 432 being generated along the datum line 428, thereby decreasing the granularity. Conversely, a smaller value for the offset interval results in a greater number of planes 432 being generated along the datum line 428, thereby increasing the granularity. Additionally, while the accuracy of the axis line 438 generated in the procedure 330 generally increases with a reduction in granularity, the increase in accuracy may not necessarily be proportional to the corresponding increase in computational requirements. For example, the relationship between the cost of additional computational requirements and the benefit of increased accuracy may be subject to diminishing returns. Thus, the cost-benefit ratio may be optimized by selecting an appropriate value for the offset interval, which may include one or more of the following techniques.

In certain forms, the offset interval between adjacent planes 432 may be a predetermined value, and the number of planes 432 generated may depend upon the length of the datum line 428. In other forms, the number of planes 432 generated may be a predetermined value, and the offset interval between adjacent planes 432 may depend upon the length of the datum line 428. In further forms, the number of planes 432 and/or the offset interval may be selected based upon other criteria, such as user preferences which may be input during the parameter procedure 320. As described in further detail below, the process 300 may include more than one iteration of the axis line procedure 330. In certain embodiments, the plane angle and/or the offset interval may remain constant within a given iteration and/or remain constant for multiple iterations. In certain embodiments, the plane angle and/or the offset interval may vary within a given iteration and/or vary from one iteration to the next. For example, the plane angle and/or the offset angle may remain constant within each iteration while varying from one iteration to the next.

The procedure 330 also includes an operation 334, which includes determining a plurality of contours 434. Each contour 434 corresponds to one of the planes 432, and is defined as the intersection between the corresponding plane 432 and at least a portion of the intercondylar surface model 402. In the illustrated form, each contour 434 is defined at the intersection of the corresponding plane 432 and the cropped model 403. For example, in FIG. 7, the contour 434a is defined at the intersection of the plane 432a and the cropped model 403. In other embodiments, a contour 434 may not necessarily be defined by the entire intersection between the corresponding plane 432 and the entire cropped model 403, and may instead be defined by the intersection between the corresponding plane 432 and the intercondylar surface model 402.

The procedure 330 also includes an operation 336, which includes generating a plurality of saddle points 436. Each of the saddle points 436 corresponds to one of the contours 434, and is defined at a local extremum of the corresponding contour 434. The operation 336 may, for example, include calculating the local minimum of each contour 434 on the corresponding plane 432, and generating each of the saddle points 436 at the corresponding one of the local minima. For example, in FIG. 7, the saddle point 436a is defined at a local minimum of the contour 434a, which in the illustrated embodiment happens to coincide with the user-selected point 427a. In certain embodiments, generating a saddle point 436 may include determining one or more of the following points: the point at which the derivative of the corresponding contour 434 is equal to zero; the point at which the corresponding contour 434 is perpendicular to the datum line 428; the point at which the distance between the corresponding contour 434 and the datum line 428 is the smallest. The operation 336 may further include storing information representative of the saddle points 436, such as information relating to the positions of the saddle points 436 with reference to a three-dimensional coordinate system.

The procedure 330 further includes an operation 338, which includes generating a straight axis line 438 based upon the saddle points 436. The operation 338 may include generating the axis line 438 such that the axis line 438 fits the saddle points 436. For example, the axis line 438 may be generated as a line of best fit for the saddle points 436, such as by applying linear regression techniques to the coordinates of the saddle points 436.

With the axis line 438 generated, the process 300 may continue to the iterative procedure 340. The iterative procedure 340 may include an operation 342, which includes generating an iteration criterion 343 related to at least one feature of the axis line procedure 330. In certain embodiments, the iteration criterion 343 may relate to the datum line 428, one or more of the planes 432, one or more of the contours 434, one or more of the saddle points 436, and/or the axis line 438. By way of example, the iteration criterion 343 may take the form of an equation or a series of points describing the axis line 438. In certain embodiments, the iteration criterion 343 may relate to a statistical correlation between the saddle points 436 and the axis line 438. In such forms, the operation 342 may include calculating a correlation value indicative of the statistical correlation between the saddle points 436 and the axis line 438, such as a correlation coefficient (R) or a coefficient of determination ($R^2$). In certain embodiments, the iteration criterion 343 may be indicative of the number of iterations performed thus far.

The iterative procedure 340 further includes a conditional 344, which includes determining whether or not to perform an additional iteration of the axis procedure 330 based upon a comparison of the iteration criterion 343 with a comparison criterion 345. The conditional 344 may yield a negative first result 344N when the comparison indicates that an additional iteration of the axis procedure 330 need not be performed, and may yield a positive second result 344Y when the comparison indicates that an additional iteration of the axis procedure 330 is warranted. In certain embodiments, the conditional 344 may yield the negative result 344N when the iteration criterion 343 satisfies the comparison criterion 345; in other embodiments, the conditional 344 may yield the negative result 344N when the iteration criterion 343 violates the comparison criterion 345. In response to the negative result 344N, the process 300 may continue to the AP axis procedure 350. In response to the positive result 344Y, the process 300 may continue to an operation 346, which is described in further detail below.

In certain forms, the iteration criterion 343 may include the correlation value, and the comparison criterion 345 may include a threshold value indicative of a sufficient correlation between the saddle points 436 and the axis line 438. In other words, the threshold value may indicate that the axis line 438 fits the saddle points 436 with an acceptable accuracy. In such forms, the conditional 344 may return the positive result 344Y when the correlation value of the iteration criterion 343 fails to meet the threshold value of the comparison criterion 345, thereby indicating that another iteration is warranted. Conversely, the conditional 344 may return the negative result 344N when the correlation value of the iteration criterion 343 meets the threshold value of the comparison criterion 345, thereby indicating that the axis line 438 sufficiently matches the saddle points 436 and that the additional iteration is not warranted.

In certain forms, the comparison criterion 345 may include the iteration criterion 343 of a prior iteration of the axis procedure 330, and may further include a threshold value indicative of a sufficient correlation between the iteration criteria 343 of the current and prior iterations of the axis procedure 330. In such embodiments, the threshold value may indicate that the change in the iteration criterion 343 from the prior iteration to the current iteration is sufficiently small, thereby indicating that the process 300 has converged on a solution. For example, the iteration criterion 343 may be representative of the axis line 438, and the conditional 344 may include determining an angular and/or spatial offset between the axis line 438 of the current iteration and the axis line 438 of the prior iteration. An offset violating the threshold of the comparison criterion 345 may indicate that the process 300 has not yet converged sufficiently. The conditional 344 may accordingly yield the positive result 344Y, thereby indicating that an additional iteration is warranted. Conversely, an offset satisfying the threshold of the comparison criterion 345 may indicate that the process 300 has sufficiently converged on a solution, and that additional iterations are not warranted. The conditional 344 may accordingly yield the negative result 344N, thereby indicating that additional iterations are not warranted.

In certain forms, the iteration criterion 343 may be representative of the number of iterations performed, and the comparison criterion 345 may include a threshold value for the number of iterations performed thus far in the process 300. In other words, the feature to which the iteration criterion 343 relates may be the iteration number of the iteration. In such embodiments, the conditional 344 may yield the positive result 344Y when the number of iterations performed falls below the threshold value, and may yield the negative result 344N when the number of iterations performed meets or exceeds the threshold value.

In certain forms, the iteration criterion 343 and/or the comparison criterion 345 may include multiple criteria, and the conditional 344 may be based upon a comparison of the multiple criteria. For example, the iteration criterion 343 may include the correlation value and the number of iterations performed, and the comparison criterion 345 may include threshold values for the correlation value and the number of iterations performed. In this example, the conditional 344 may include comparing the correlation value and the number of iterations performed to the threshold values, and yielding the negative result 344N when either the correlation value or the number of iterations performed satisfies the corresponding threshold of the comparison criterion 345.

In certain forms, the conditional 344 may yield the negative result 344N when a predetermined number of the iteration criteria 343 satisfy the corresponding one of the comparison criteria 345. In certain forms, the conditional 344 may yield the positive result 344Y when a predetermined number of the iteration criteria 343 violate the corresponding one of the comparison criteria 345. Additionally, one or more of the comparison criteria 345 may be designated as a necessary criterion or a sufficient criterion, and the conditional 344 may include evaluating the necessity and/or sufficiency of one or more satisfied comparison criteria 345.

Figure 8:
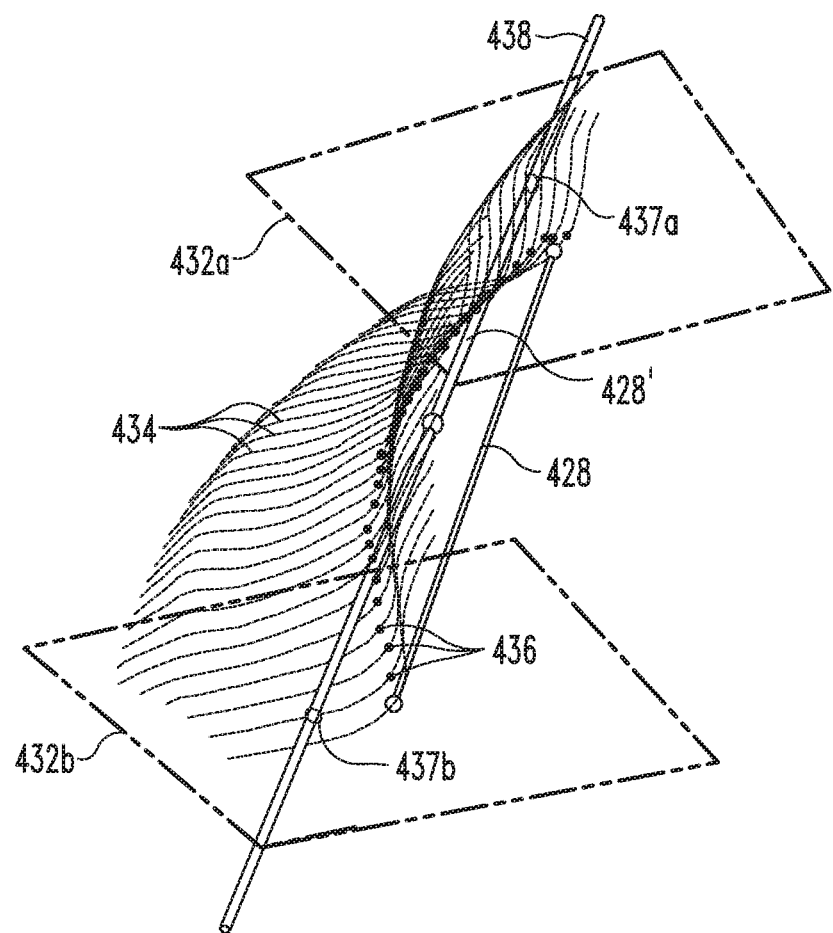
FIG. 8 illustrates the planes, contours, and saddle points of FIG. 7 along with an axis line.
Figure 8:
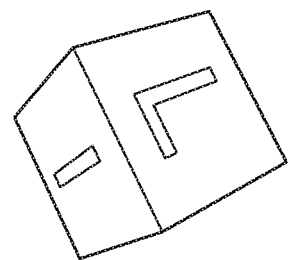
Figure 9:
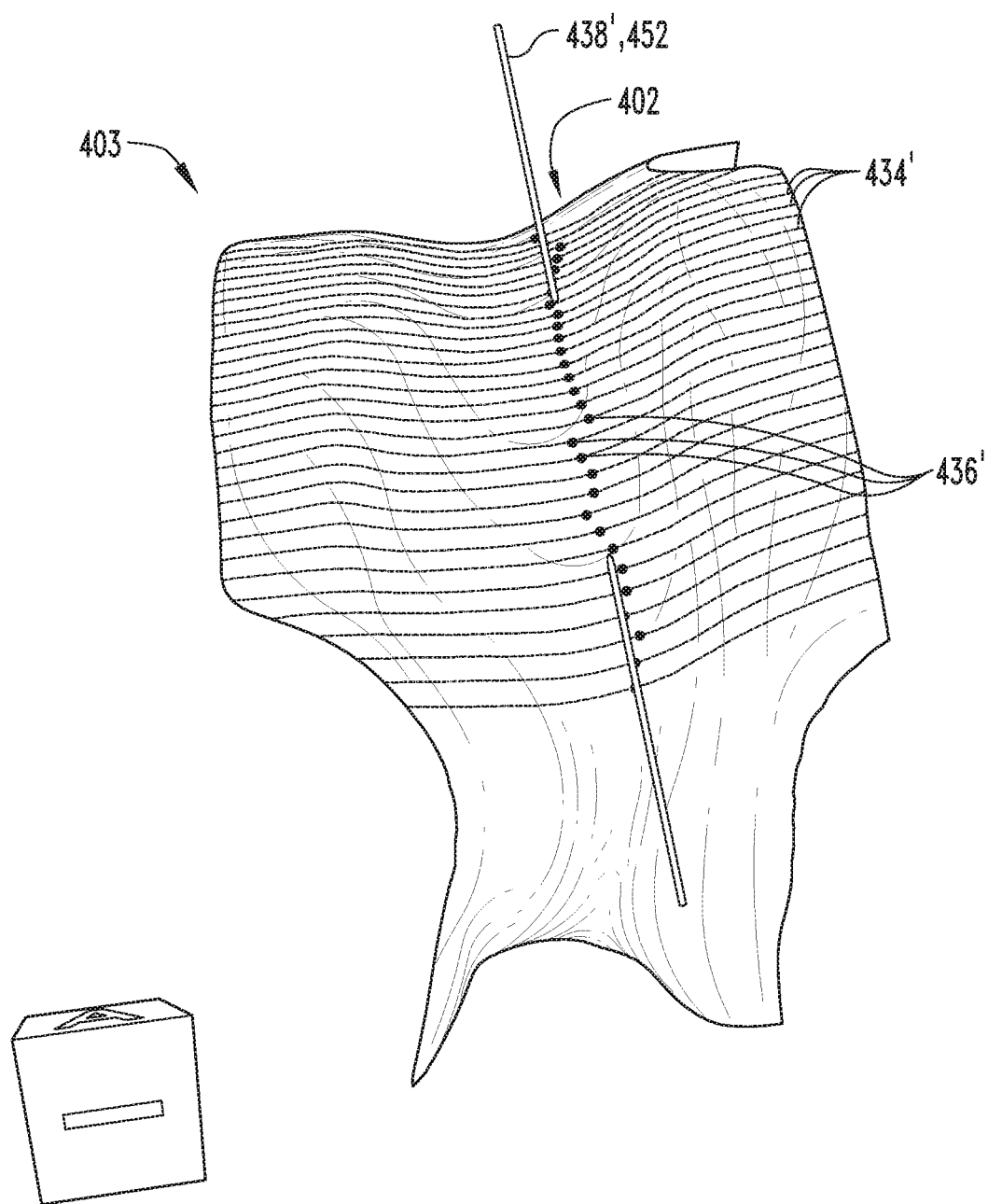
FIG. 9 illustrates the cropped model of FIG. 4 along with revised contours saddle points and a revised axis line.

As noted above, the process 300 may continue to the operation 346 in response to the positive result 344Y of the conditional 344. The operation 346 includes generating a new datum line 428 based upon the axis line 438 of the most recent iteration. The operation 346 may include determining the points at which the outermost planes 432 intersect the axis line 438, and defining the new datum line 428 between the points of intersection. For example, FIG. 8 illustrates a point 437a at which the plane 432a intersects the axis line 438, a point 437b at which the plane 432b intersects the axis line 438, and a new datum line 428' extending between the points 437a, 437b. With the new datum line 428' generated, the process 300 may return to the operation 332 to perform an additional iteration of the axis procedure 330 using the new datum line 428' as the datum line 428, thereby generating a new or updated axis line 438'. For example, FIG. 9 illustrates the cropped model 403 along with contours 434', saddle points 436', and an axis line 438' resulting from an additional iteration of the axis line procedure 330.

As additional iterations of the axis line procedure 330 are performed, the generated axis lines 438 may begin to converge, thereby indicating that the process 300 is approaching a final solution for the AP axis 452. As noted above, the iterative procedure 340 may involve determining whether the iterations of the axis line procedure 330 have converged on such a solution based upon the iteration criterion 343 and the comparison criterion 345, and the comparison criterion 345 may include the iteration criterion 343 of a previously-performed iteration of the axis line procedure 330 and a threshold criterion. Additionally, the conditional 344 may include determining a delta value indicative of a change between the iteration criteria 343 of the current and previously-performed iterations, and comparing the delta value with the threshold criterion to determine whether or not an additional iteration is warranted. By way of example, the conditional 344 may include determining a delta value indicative of a change in the axis lines 438 generated in the current and previous iterations, and determining that an additional iteration is warranted when the delta value exceeds the threshold. Further examples relating to determining the convergence of the iterations are provided above.

After the axis line 438 has been generated and possibly updated, the process 300 may continue to the AP axis procedure 350. The procedure 350 includes an operation 352, which includes generating an AP axis 452 based upon the axis line 438. The operation 352 may include generating the AP axis 452 as the axis line 438, a segment of the axis line 438, or an extension of the axis line 438. The procedure 350 may further include an operation 354, which includes outputting information relating to the AP axis 452. By way of example, the operation 354 may include displaying the AP axis 452 along with the cropped model 403 (as illustrated in FIG. 9) or the distal femur model 400. As another example, the operation 354 may include updating the distal femur model 400 to include the AP axis 452, and sending the updated model 400 to the server 240.

In certain forms, the AP axis procedure 350 may include displaying the AP axis 452 at the display device 216, and prompting the user to indicate whether successive iterations of the parameter procedure 320 and/or the axis line procedure 330 are desired. If the user indicates that successive iterations are desired, the process 300 may include returning to the operation or procedure corresponding to the user's selection. Subsequent iterations may, for example, include displaying information from a previous iteration, such as the selection box 423, the selected points 427a, 427b, the datum line 428, the axis line 438, and/or the AP axis 452. By way of example, a subsequent iteration of the parameters procedure 320 may include displaying the selection box 423 and/or selected points 427a, 427b, and enabling the user to move, manipulate, or otherwise modify the selection box 423 and/or selected points 427a, 427b.

While not specifically illustrated in FIG. 3, it is to be appreciated that the process 300 may include performing validation procedures for one or more of the operations. A validation procedure may, for example, include verifying whether an input is valid, and when the input is determined to be invalid, informing the user that the input is invalid and/or prompting the user to provide a new input. For example, the parameter procedure 320 may include determining the validity of the cropping information 323 received in the operation 322, and prompting the user to form a new cropping box 423 if the cropping information 323 is invalid. Validating the cropping information 323 may, for example, include determining whether the selection includes a sufficient portion of the intercondylar surface model 402 to produce accurate results in the axis line procedure 330. The parameter procedure 320 may additionally or alternatively include validating the point selection information 327 received in the operation 326, and prompting the user to reselect one or both of the points 427a, 427b if the point selection information 327 is invalid. Validating the point selection information 327 may, for example, include verifying that the selected points 427a, 427b are located on the intercondylar surface model 402 and/or ensuring a minimum distance between the points 427a, 427b.

Additionally, one or more of the operations may include outputting image information for display and inspection by the user, such as at the display device 216. As noted above, FIGS. 4-9 illustrate exemplary stages of the process 300. In certain forms, images corresponding to one or more of the Figures may be output to the display device 216 at an appropriate time during the process 300. In other embodiments, one or more of the intermediate stages may not necessarily be displayed to the user. For example, the planes 432 may not necessarily be displayed during the operation 332, and the contours 434 may not necessarily be displayed during the operation 334. Furthermore, "generating" a feature need not include generating image data relating to the feature, and may instead include calculating values, equations, or other descriptions related to the feature. For example, generating the planes 432 may include determining equations describing the planes 432, and generating the contours 434 may include determining the intersections of the planes 432 and the cropped model 403 based upon the equations and the surface model data.

Once a satisfactory AP axis 452 has been generated and output to the user interface 213, the AP axis line 452 and the distal femur model 400 may be utilized in various surgical planning procedures. As noted above, the rotational position of the distal femur 100 about the AP axis 119 has a measurable effect on the outcome of the planned surgery. Accordingly, certain methods may include rotating the distal femur model 400 about the determined AP axis 452 to obtain a desired orientation for the femur of the particular patient. By way of example, a method may include displaying the distal femur model 400 along with a model of the patient's tibia, and enabling the surgeon to rotate the distal femur model 400 about the AP axis 452 to obtain a desired orientation. In certain embodiments, the desired orientation may correspond to a desired value for the varus-valgus angle of the femur. In certain forms, the method may further include comparing a mechanical axis of the femur to a mechanical axis of the tibia to determine the varus-valgus angle, and displaying the varus-valgus angle as the user rotates the distal femur model 400 about the AP axis 452. Once an appropriate orientation of the distal femur model 400 is selected, the model 400 may be updated with information relating to the selected orientation. The updated model may be utilized in other steps of the surgical planning process, such as selecting or designing an appropriate orthopedic implant to be used during the procedure. By way of example, the updated model may be utilized to design a patient-specific orthopedic implant tailored to the distal femur 100 of the particular patient.

As is evident from the foregoing, the process 300 provides an interactive method for determining the AP axis 452 by enabling the user to input the cropping information 323 and/or point selection information 427. While certain techniques may enable for a more fully-automated generation of an AP axis, these results often must be reviewed by the user for validation. If the user has had no input into the generation of the AP axis, it may be difficult for the user to determine whether the generated AP axis is accurate. By enabling the user to input an initial estimate for the AP axis (e.g., by selecting the points 427 for the initial datum line 428), the process 300 may facilitate the validation process by allowing the user to compare the initial estimate (e.g., the initial datum line 428) to the final AP axis 452. Additionally, the process 300 may be relatively insensitive to the user's initial estimate, for example as a result of updating the datum line 428 for each successive iteration of the axis line procedure 430. Thus, the process 300 may provide for more robust and accurate determination of the AP axis 119.

As noted above, the process 300 may further include a surgical tool procedure 360, which generally involves designing and optionally manufacturing a patient-specific surgical tool 369. By way of example, the surgical tool 369 may be a cutting block or a femoral prosthesis. The procedure 360 may include an operation 362, which includes determining at least one additional axis of the distal femur 100. The operation 362 may, for example, include determining one or more of the TEA 180, the PCA 190, a mechanical axis of the femur 100, and an anatomic axis of the femur 100. In certain forms, the at least one additional axis may be determined using manual and/or automated techniques known in the art, which need not be described in detail herein. The operation 362 further includes generating axis information 363 relating to the AP axis 119 and the at least one additional axis. The operation 362 may further include rotating the model 400 about one or more of the additional axes to adjust the orientation of the model 400, and the axis information 363 may include information relating to the rotation of the model 400 about the one or more of the additional axes.

The procedure 360 further includes an operation 364, which includes generating resection plane information 365 based at least in part upon the axis information 363. The resection plane information 365 relates to at least one resection cut to be performed on the distal femur 100 during a surgical procedure, such as a total knee arthroplasty (TKA) procedure. The resection plane information 365 may include information relating to the orientation of the one or more resection planes in relation to the distal femur model 400. In certain forms, the at least one resection plane may be determined using manual and/or automated techniques known in the art, which need not be described in detail herein.

The procedure 360 also includes an operation 366, which includes generating a surgical tool model 367 based at least in part upon the resection plane information 365. In certain forms, generation of the surgical tool model 367 may further be based upon the distal femur model 400. For example, the model 367 may be a model of a patient-specific cutting block, and the operation 366 may include generating the cutting block model 367 with cutting slots aligned with the at least one resection plane identified in the operation 364. In such forms, the operation 366 may further include generating the cutting block model 367 with contact surfaces contoured to match the condyles 112, 114 and/or the intercondylar region 115. As another example, the model 367 may be a model of a patient-specific femoral prosthesis, and the operation 366 may include generating the femoral prosthesis model 367 with bone-facing surfaces corresponding to the at least one resection plane identified in the operation 364. In such forms, the operation 366 may further include generating the femoral prosthesis model 367 with an outer surface corresponding to the outer surface of a portion of the distal femur model 400.

The procedure 360 may further include an operation 368, which includes manufacturing a patient-specific surgical tool 369 according to the model 367. In certain forms, the operation 368 may include generating a mold corresponding to the model 367, and manufacturing the tool 369 using the mold, for example using injection-molding or casting techniques. In certain forms, the operation 368 may include manufacturing the surgical tool 369 using a rapid manufacturing technique such, as additive manufacturing. By way of example, the operation 368 may include manufacturing the tool 369 using a three-dimensional printing technique, for example when the tool 369 is an orthopedic cutting block. As another example, the operation 368 may include manufacturing the tool 369 using a selective laser sintering technique, for example when the tool 369 is a femoral prosthesis.

Figure 10:
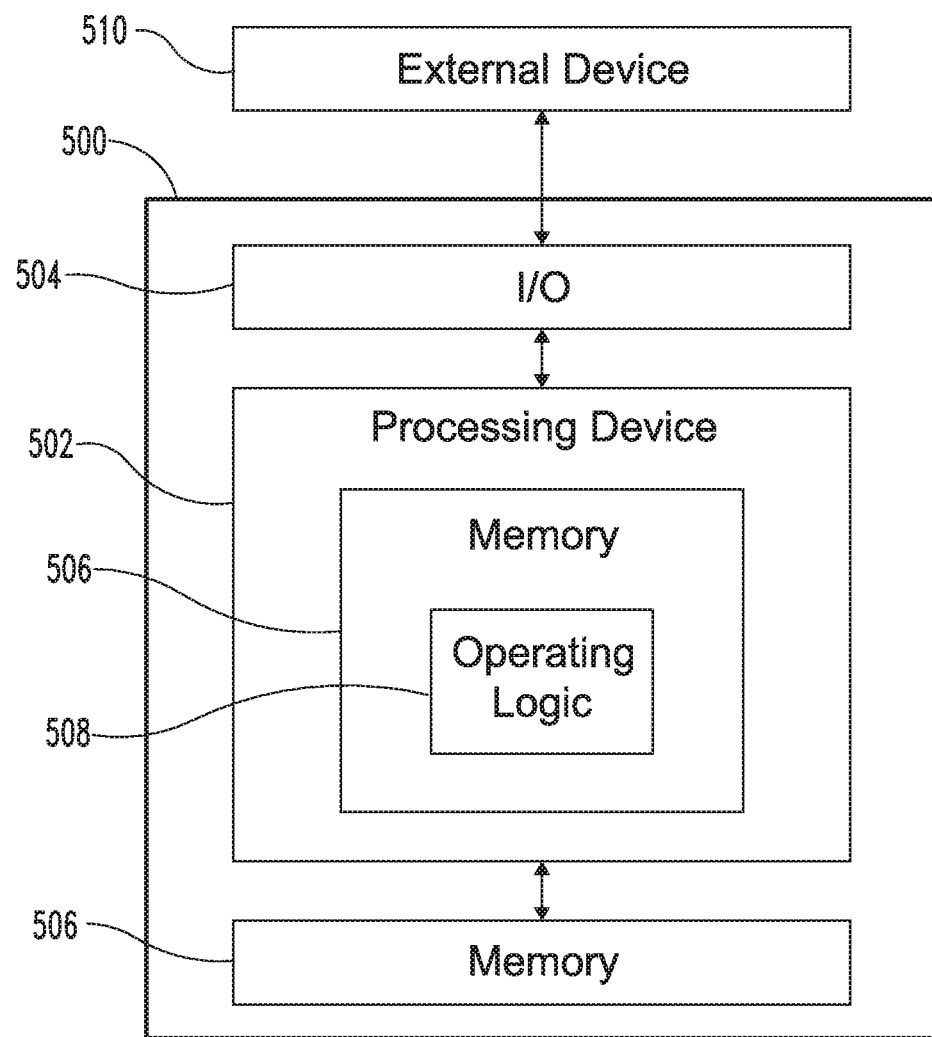
FIG. 10 is a schematic block diagram of a computing device which may be utilized in connection with certain embodiments.

FIG. 10 is a schematic block diagram of a computing device 500. The computing device 500 is one example of a computer, server, mobile device, or equipment configuration which may be utilized in connection with the design device 210, design tool 220, server 240, or modeling tools 250 illustrated in FIG. 2. The computing device 500 includes a processing device 502, an input/output device 504, memory 506, and operating logic 508. Furthermore, the computing device 500 communicates with one or more external devices 510.

The input/output device 504 allows the computing device 500 to communicate with the external device 510. For example, the input/output device 504 may be a network adapter, network card, interface, or a port (e.g., a USB port, serial port, parallel port, an analog port, a digital port, VGA, DVI, HDMI, FireWire, CAT 5, or any other type of port or interface). The input/output device 504 may be comprised of hardware, software, and/or firmware. It is contemplated that the input/output device 504 may include more than one of these adapters, cards, or ports.

The external device 510 may be any type of device that allows data to be inputted or outputted from the computing device 500. For example, the external device 510 may be a mobile device, a reader device, equipment, a handheld computer, a diagnostic tool, a controller, a computer, a server, a printer, a display, an alarm, an illuminated indicator such as a status indicator, a keyboard, a mouse, or a touch screen display. Furthermore, it is contemplated that the external device 510 may be integrated into the computing device 500. It is further contemplated that there may be more than one external device in communication with the computing device 500.

The processing device 502 can be of a programmable type, a dedicated, hardwired state machine, or a combination of these; and can further include multiple processors, Arithmetic-Logic Units (ALUs), Central Processing Units (CPUs), Digital Signal Processors (DSPs) or the like. For forms of processing device 502 with multiple processing units, distributed, pipelined, and/or parallel processing can be utilized as appropriate. The processing device 502 may be dedicated to performance of just the operations described herein or may be utilized in one or more additional applications. In the depicted form, the processing device 502 is of a programmable variety that executes algorithms and processes data in accordance with operating logic 508 as defined by programming instructions (such as software or firmware) stored in memory 506. Alternatively or additionally, the operating logic 508 for processing device 502 is at least partially defined by hardwired logic or other hardware. The processing device 502 can be comprised of one or more components of any type suitable to process the signals received from input/output device 504 or elsewhere, and provide desired output signals. Such components may include digital circuitry, analog circuitry, or a combination of both.

The memory 506 may be of one or more types, such as a solid-state variety, electromagnetic variety, optical variety, or a combination of these forms. Furthermore, the memory 506 can be volatile, nonvolatile, or a combination of these types, and some or all of memory 506 can be of a portable variety, such as a disk, tape, memory stick, cartridge, or the like. In addition, the memory 506 can store data that is manipulated by the operating logic 508 of the processing device 502, such as data representative of signals received from and/or sent to the input/output device 504 in addition to or in lieu of storing programming instructions defining the operating logic 508, to name just one example. As shown in FIG. 10, the memory 506 may be included with the processing device 502 and/or coupled to the processing device 502.

The processes in the present application may be implemented in the operating logic 508 as operations by software, hardware, artificial intelligence, fuzzy logic, or any combination thereof, or at least partially performed by a user or operator. In certain embodiments, units represent software elements as a computer program encoded on a non-transitory computer readable medium, wherein the design device 210, design tool 220, server 240, or modeling tool 250 performs the described operations when executing the computer program.

Certain embodiments of the present disclosure relate to a computer-implemented method comprising: a) performing a modeling procedure with a computing device, wherein the modeling procedure comprises: i) the computing device receiving information relating to a distal femur of a particular patient, wherein the distal femur includes an intercondylar surface; ii) the computing device generating a distal femur model based upon the received information, wherein the distal femur model is representative of at least a portion of the distal femur, and wherein the distal femur model includes an intercondylar surface model representative of the intercondylar surface; and iii) the computing device outputting to a user interface information relating to the distal femur model; b) performing a parameters procedure with the computing device, the parameters procedure comprising: i) the computing device receiving, from the user interface, point selection information including information relating to a user-selected first point on the intercondylar surface model and information relating to a user-selected second point on the intercondylar surface model; and ii) the computing device generating a datum line based upon the point selection information, wherein the datum line extends between the first point and the second point; c) performing an iteration of an axis line procedure with the computing device, wherein each iteration of the axis line procedure comprises: i) the computing device generating a plurality of planes, wherein each of the planes intersects the datum line and the intercondylar surface model; ii) the computing device generating a plurality of contours, wherein each of the contours corresponds to one of the planes and is defined by an intersection of the corresponding plane with the intercondylar surface model; iii) the computing device generating a saddle point set, wherein generating the saddle point set includes determining a saddle point for each of the contours; and iv) the computing device generating an axis line based upon the saddle point set, wherein generating the axis line includes fitting the axis line to the saddle point set; and d) performing an anterior-posterior (AP) axis procedure with the computing device, wherein the AP axis procedure comprises: i) the computing device determining an AP axis of the distal femur based upon the axis line; and ii) the computing device outputting to the user interface information relating to the determined AP axis.

In certain embodiments, the AP axis procedure further comprises the computing device outputting to the user interface information relating to the distal femur model, and displaying the AP axis and the distal femur model at the user interface.

In certain embodiments, the method further comprises e) performing at least one iterative procedure subsequent to performing the axis line procedure and prior to performing the AP axis procedure, wherein each iterative procedure comprises: i) the computing device generating an updated datum line based upon the axis line of a previously-performed iteration of the axis line procedure; and ii) the computing device performing an additional iteration of the axis line procedure using the updated datum line; wherein determining the AP axis of the distal femur based upon the axis line includes determining the AP axis of the distal femur based upon the axis line generated in a most recent of the additional iterations of the axis line procedure.

In certain embodiments, each iterative procedure further comprises iii) the computing device comparing a result of the additional iteration of the axis line procedure to a corresponding result of the previously-performed iteration of the axis line procedure; and performing at least one iterative procedure further comprises: the computing device performing another of the iterative procedures in response to a first result of the comparing; and the computing device proceeding to the AP axis procedure in response to a second result of the comparing.

In certain embodiments, the first result of the comparing is indicative of the result of the additional iteration of the axis line procedure being different from the corresponding result of the previously-performed iteration of the axis line procedure by at least a threshold difference, and the second result of the comparing is indicative of the result of the additional iteration of the axis line procedure being similar to the corresponding result of the previous-performed iteration of the axis line procedure within the threshold difference.

In certain embodiments, the result of the additional iteration of the axis line procedure includes information related to the axis line generated in the additional iteration of the axis line procedure, and the result of the previously-performed iteration of the axis line procedure includes the axis line generated in the previously-performed iteration of the axis line procedure.

In certain embodiments, each iteration of the axis line procedure further comprises the computing device generating an iteration criterion relating to at least one feature of the iteration, and each iterative procedure further comprises: iii) the computing device comparing the iteration criterion of the additional iteration of the axis line procedure with a comparison criterion; and iv) the computing device selectively performing another iterative procedure based upon the comparing.

In certain embodiments, the iteration criterion includes a correlation value indicative of a correlation between the axis line and the saddle points, and the comparison criterion includes a correlation threshold value.

In certain embodiments, for each iterative procedure, the comparison criterion further includes the correlation value of the previously-performed iteration of the axis line procedure.

In certain embodiments, each iteration of the axis line procedure further comprises: v) the computing device generating an iteration criterion relating to at least one feature of the iteration; vi) the computing device comparing the iteration criterion to a comparison criterion; and vii) the computing device selectively performing an iterative procedure based upon the comparing; wherein the iterative procedure comprises: i) the computing device generating an updated datum line based upon the axis line of a previously-performed iteration of the axis line procedure; and ii) the computing device performing an additional iteration of the axis line procedure using the updated datum line.

In certain embodiments, the parameters procedure further comprises the computing device receiving cropping information from the user interface, and the computing device generating a cropped model including the intercondylar surface model, wherein generating the cropped model comprises cropping the distal femur model based upon the cropping information.

In certain embodiments, the AP axis procedure further comprises the computing device outputting to the user interface information relating to the cropped model, and the user interface displaying the AP axis along with the cropped model.

In certain embodiments, generating the planes includes generating each plane at a predetermined angle with respect to the datum line.

In certain embodiments, generating the planes includes generating the planes at a constant offset interval along the datum line.

In certain embodiments, determining a saddle point for each of the contours includes determining a local minimum for each contour and defining the saddle points at the local minima.

Certain embodiments of the present disclosure relate to a method comprising: receiving by a computing device information relating to a distal femur model including an intercondylar surface model, wherein the distal femur model is representative of at least a portion of a distal femur of a particular patient and includes an intercondylar surface model representative of an intercondylar surface of the distal femur of the particular patient; displaying at a user interface the distal femur model; receiving by the computing device cropping information from the user interface, the cropping information corresponding to a user-selected portion of the distal femur model; generating by the computing device a cropped model including the user-selected portion of the distal femur model, wherein generating the cropped model includes cropping the distal femur model based upon the cropping information; displaying at the user interface the cropped model; receiving by the computing device point selection information from the user interface, the point selection information corresponding to a user-selected first point on the intercondylar surface model and a user-selected second point on the intercondylar surface model; generating by the computing device a datum line extending between the user-selected first point and the user-selected second point; performing by the computing device at least one iteration of an axis line procedure, wherein each iteration of the axis line procedure comprises: generating by the computing device a plurality of planes, wherein each of the planes defines a plane angle with respect to the datum line, wherein each of the planes is offset from an adjacent plane by an offset interval, and wherein each of the planes intersects the intercondylar surface model at an intersection; generating by the computing device a plurality of contours, wherein each of the contours is defined by the intersection of the intercondylar surface model and a corresponding one of the planes; generating by the computing device a plurality of saddle points, wherein each of the saddle points is defined at a local extremum of a corresponding one of the contours; generating by the computing device an axis line based upon the plurality of saddle points, wherein generating the axis line includes fitting a straight line to the plurality of saddle points; generating by the computing device an iteration criterion relating to at least one feature of the iteration; and determining by the computing device whether or not to perform an additional iteration based upon the iteration criterion and a comparison criterion; in response to determining to perform the additional iteration: generating by the computing device an updated datum line based upon the axis line; and performing the additional iteration using the updated datum line; and in response to determining not to perform the additional iteration: generating by the computing device an anterior-posterior axis for the distal femur based upon the axis line; and displaying at the user interface the anterior-posterior axis and at least a portion of the distal femur model.

In certain embodiments, each iteration of the axis line procedure further comprises determining by the computing device a correlation value indicative of a statistical correlation between the axis line and the saddle points, and generating by the computing device the iteration criterion based upon the correlation value.

In certain embodiments, the correlation value is one of a correlation coefficient and a coefficient of determination.

In certain embodiments, the comparison criterion includes a threshold value for the correlation value.

In certain embodiments, the comparison criterion relates to at least one of the axis line, the saddle points, and a correlation between the axis line and the saddle points.

In certain embodiments, the plane angle is constant within each iteration of the axis line procedure.

In certain embodiments, the plane angle is a right angle, and each of the planes is orthogonal to the datum line.

In certain embodiments, the offset interval between adjacent planes is constant within each iteration of the axis line procedure.

In certain embodiments, the offset interval between adjacent planes is constant for each iteration of the axis line procedure.

In certain embodiments, each iteration of the axis line procedure comprises generating the same number of planes, and the offset interval for each iteration depends in part upon a length of the datum line for the iteration.

In certain embodiments, performing at least one iteration of the axis line procedure includes performing by the computing device a plurality of the iterations, wherein the plurality of iterations includes a prior iteration and a subsequent iteration, and wherein the comparison criterion of the subsequent iteration includes the iteration criterion of the prior iteration.

In certain embodiments, the comparison criterion of the subsequent iteration further includes a threshold, and in the subsequent iteration, determining whether to perform the additional iteration includes determining a change between the iteration criterion of the prior iteration and the iteration criterion of the subsequent iteration, and comparing the change to the threshold.

In certain embodiments, the method further comprises determining by the computing device at least one additional axis of the distal femur model, determining by the computing device at least one resection plane based at least in part upon the AP axis and the at least one additional axis, and generating by the computing device a surgical tool model based at least in part upon the at least one resection plane.

In certain embodiments, the at least one additional axis of the distal femur model includes a transepicondylar axis and a posterior condylar axis.

In certain embodiments, the surgical tool model is a cutting block model, and generating the cutting block model includes generating the cutting block model with at least one cutting slot aligned with the at least one resection plane.

In certain embodiments, the surgical tool model is a femoral prosthesis model, and generating the femoral prosthesis model includes generating the femoral prosthesis model with at least one bone-facing surface corresponding to the at least one resection plane.

In certain embodiments, the method further comprises manufacturing the surgical tool based upon the surgical tool model.

In certain embodiments, manufacturing the surgical tool includes manufacturing the tool using a rapid manufacturing technique.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A computer-implemented method for adjusting a varus-valgus angle in a surgical plan for a distal femur of a patient, the method comprising:
   obtaining a three-dimensional model of the distal femur of the patient including an intercondylar surface;
   identifying, based on user input, a datum line comprising at least two points on the intercondylar surface;
   performing one or more iterative revisions, wherein each iterative revision comprises:
   generating a plurality of planes, each plane forming a predetermined angle with the datum line and intersecting the intercondylar surface, identifying a saddle point of the intercondylar surface on each of the plurality of planes, thereby forming a saddle point set, and calculating a fitted line for the saddle point set, wherein the datum line is re-defined as the fitted line for a subsequent iterative revision;

generating an anterior-posterior (AP) axis based on the fitted line;

rotating the three-dimensional model about the AP axis to alter an orientation of the three-dimensional model, thereby adjusting the varus-valgus angle of the distal femur; and updating the surgical plan based on the altered orientation of the three-dimensional model;

wherein each iterative revision further comprises assessing whether to perform a subsequent iterative revision based on at least one iteration criterion.

2. The method of claim 1, further comprising cropping, based on cropping input, the three-dimensional model to obtain a cropped three-dimensional model including the intercondylar surface.

3. The method of claim 1, wherein the one or more iterative revisions comprise a plurality of iterative revisions, wherein the AP axis is generated based on the fitted line of a final iterative revision.

4. The method of claim 1, wherein the user input comprises a first user-identified point and a second user-identified point on the intercondylar surface.

5. The method of claim 1, wherein the three-dimensional model is based on anatomical information related to the distal femur of the patient.

6. The method of claim 5, wherein the anatomical information comprises one or more of an x-ray image, an MRI image, a CT image, a CAD model, and information received via an input device.

7. The method of claim 5, further comprising generating, based on the anatomical information, the three-dimensional model.

8. The method of claim 1, wherein each plane is orthogonal to the datum line.

9. The method of claim 1, wherein the plurality of planes are substantially equally spaced along the datum line according to a predetermined offset interval.

10. The method of claim 1, wherein identifying a saddle point for each plane comprises:
identifying a contour of the intercondylar surface on the plane; and
calculating the saddle point as a local minimum point on the contour.

11. The method of claim 1, wherein the at least one iteration criterion comprises one or more of:
a correlation value between the saddle point set and the fitted line of the iterative revision;
a number of completed iterative revisions; and
a correlation value between the fitted line of at least two successive iterative revisions.

12. The method of claim 1, wherein the AP axis comprises one or more of the fitted line, a segment of the fitted line, and an extension of the fitted line.

13. The method of claim 1, further comprising designing a patient-specific surgical tool based on at least the updated surgical plan.

14. The method of claim 13, wherein the patient-specific surgical tool comprises one or more of a prosthetic implant and a cutting block.

15. A system for adjusting a varus-valgus angle in a surgical plan for a distal femur of a patient, the system comprising:
a display device;
an input device;
at least one processor; and
at least one computer-readable medium coupled to the at least one processor storing instructions that, when executed by the at least one processor, cause the system to:
display, on the display device, a three-dimensional model of the distal femur of the patient including an intercondylar surface,
receive, from the input device, user input comprising at least two points on the intercondylar surface, thereby defining a datum line;
perform a plurality of iterative revisions, wherein each of the plurality of iterative revisions comprises:
generating a plurality of planes, each plane forming a predetermined angle with the datum line and intersecting the intercondylar surface,
identifying a saddle point of the intercondylar surface on each of the plurality of planes, thereby forming a saddle point set, and
calculating a fitted line for the saddle point set, wherein the datum line is re-defined as the fitted line for a subsequent iterative revision;
generate an anterior-posterior (AP) axis based on the fitted line;
rotate the three-dimensional model about the AP axis to alter an orientation of the three-dimensional model, thereby adjusting the varus-valgus angle of the distal femur; and
update the surgical plan based on the altered orientation of the three-dimensional model;
wherein the AP axis is generated based on the fitted line of a final iterative revision.

16. The system of claim 15, wherein the instructions, when executed by the at least one processor, further cause the system to crop, based on cropping input, the three-dimensional model to obtain a cropped three-dimensional model including the intercondylar surface.

17. The system of claim 15, wherein the user input comprises a first user-identified point and a second user-identified point on the intercondylar surface.

18. The system of claim 15, wherein the three-dimensional model is based on anatomical information related to the distal femur of the patient.

19. The system of claim 18, wherein the anatomical information comprises one or more of an x-ray image, an MRI image, a CT image, a CAD model, and information received via the input device.

20. The system of claim 18, wherein the instructions, when executed by the at least one processor, further cause the system to generate, based on the anatomical information, the three-dimensional model.

21. The system of claim 15, wherein each plane is orthogonal to the datum line.

22. The system of claim 15, wherein the plurality of planes are substantially equally spaced along the datum line according to a predetermined offset interval.

23. The system of claim 15, wherein identifying a saddle point for each plane comprises:
identifying a contour of the intercondylar surface on the plane; and
calculating the saddle point as a local minimum point on the contour.

24. The system of claim 15, wherein each iterative revision further comprises assessing whether to perform a subsequent iterative revision based on at least one iteration criterion, wherein the at least one iteration criterion comprises one or more of:
 a correlation value between the saddle point set and the fitted line of the iterative revision;
 a number of completed iterative revisions; and
 a correlation value between the fitted line of at least two successive iterative revisions.

25. The system of claim 15, wherein the instructions, when executed by the at least one processor, further cause the system to design a patient-specific surgical tool based on at least the updated surgical plan.

26. The system of claim 25, wherein the patient-specific surgical tool comprises one or more of a prosthetic implant and a cutting block.

27. A system for adjusting a varus-valgus angle in a surgical plan for a distal femur of a patient, the system comprising:
 a display device;
 an input device;
 at least one processor configured to cause the system to:
  display, on the display device, a three-dimensional model of the distal femur of the patient including an intercondylar surface,
  receive, from the input device, user input comprising at least two points on the intercondylar surface, thereby defining a datum line;
  perform one or more iterative revisions, wherein each iterative revision comprises:
   generating a plurality of planes, each plane forming a predetermined angle with the datum line and intersecting the intercondylar surface,
   identifying a saddle point of the intercondylar surface on each of the plurality of planes, thereby forming a saddle point set, and
   calculating a fitted line for the saddle point set, wherein the datum line is re-defined as the fitted line for a subsequent iterative revision;
  generate an anterior-posterior (AP) axis based on the fitted line;
  rotate the three-dimensional model about the AP axis to alter an orientation of the three-dimensional model, thereby adjusting the varus-valgus angle of the distal femur; and
  update the surgical plan based on the altered orientation of the three-dimensional model;
 wherein each iterative revision further comprises assessing whether to perform a subsequent iterative revision based on at least one iteration criterion.

28. The system of claim 27, wherein the at least one iteration criterion comprises one or more of:
 a correlation value between the saddle point set and the fitted line of the iterative revision;
 a number of completed iterative revisions; and
 a correlation value between the fitted line of at least two successive iterative revisions.

\* \* \* \* \*